United States Patent [19]
Budolfsen et al.

[11] Patent Number: 5,670,192
[45] Date of Patent: Sep. 23, 1997

[54] METHOD FOR PRODUCTION OF A NON ACIDIFIED EDIBLE GEL ON MILK BASIS

[75] Inventors: Gitte Budolfsen, Frederiksberg; Per Munk Nielsen, Hillerød, both of Denmark

[73] Assignee: Novo Nordisk A/S, Bagsvaerd, Denmark

[21] Appl. No.: 436,442

[22] PCT Filed: Mar. 18, 1994

[86] PCT No.: PCT/DK94/00110

§ 371 Date: May 23, 1995

§ 102(e) Date: May 23, 1995

[87] PCT Pub. No.: WO94/21130

PCT Pub. Date: Sep. 29, 1994

[30] Foreign Application Priority Data

Mar. 19, 1993 [DK] Denmark ................. 0311/93

[51] Int. Cl.⁶ ........................................ A23C 9/12
[52] U.S. Cl. ............... 426/34; 426/42; 426/52; 426/573; 426/580
[58] Field of Search .................... 426/38, 34, 36, 426/41, 42, 52, 573, 580, 582, 583

[56] References Cited

U.S. PATENT DOCUMENTS 3,857,967  12/1974  Kikuchi et al. ................. 426/18
5,156,956  10/1992  Motoki et al. ................... 426/573
5,330,778   7/1994  Stark et al. ..................... 426/531

OTHER PUBLICATIONS

Rao, D.S., Dialog Abs. No. 1258838, Indian Dairyman, vol. 43, No. 11, pp. 514–517 (1991).

Nonaka et al., J. Food Sci., vol. 57, No. 5, pp. 1214–1241 (1992).

Ajinomoto Co. et al., Chem. Abs. No. 6095n, abstract of JP 127471 (Jan. 30, 1989).

Ajinomoto K.K., Abstract of JP, A, 58–149645 (Sep. 6, 1983).

Ikura et al., Dialog Abs. No. 1422994, Comments Agri. Food Chem., vol. 2, No. 6, pp. 389–407 (1992).

Ajinomoto K.K., JP 59–59151 (Apr. 4, 1984).

*Primary Examiner*—Leslie Wong
*Attorney, Agent, or Firm*—Steve T. Zelson, Esq.; Valeta Gregg, Esq.

[57] ABSTRACT

The method for production of a not acidified edible gel on milk basis comprises addition of transglutaminase and rennet to milk, followed by a heat treatment. Hereby a functionally and/or organoleptically satisfactory edible gel is obtained, which can be used as a mousse or pudding.

8 Claims, No Drawings

METHOD FOR PRODUCTION OF A NON ACIDIFIED EDIBLE GEL ON MILK BASIS

CROSS-REFERENCE TO RELATED APPLICATIONS

This application is a 35 U.S.C. 371 national application of PCT/DK94/00110 filed Mar. 18, 1994, which is incorporated herein by reference.

BACKGROUND FOR THE INVENTION

Many efforts have been exercised in order to generate derived milk products of nutritional value and with improved functional and/or organoleptic properties, including not acidified, edible gels on milk basis. A typical example of such products is desserts, especially mousses of different kinds, e.g. chocolate mousse and vanilla mousse. In order to prepare mousses of satisfactory quality it is necessary to add both emulsifying agents and stabilizing agents in rather large amounts.

It is the purpose of the invention to provide a method for production of a not acidified edible gel on milk basis, which exhibits satisfactory functional and/or organoleptic properties differing from the prior art not acidified edible gels on milk basis like mousses, and in relation to which it is not necessary to add any emulsifying or stabilizing agents or it is only necessary to add emulsifying or stabilizing agents in minor amounts, and a use of such gel.

SUMMARY OF THE INVENTION

The method according to the invention for production of a not acidified edible gel on milk basis is characterized by the fact that in a first step transglutaminase is added to milk or a milk like product, that in a second step rennet is added to the transglutaminase containing milk or milk like product, and that in a third step the transglutaminase and rennet containing milk or milk like product is exposed to a heat treatment.

In this specification with claims the term "milk or a milk like product" is to be understood as whole milk, skim milk, cream or a milk product with a fat content from 0% to 50% originating from any animal, preferably a cow, as such or slightly modified, e.g. by addition of flavorants. Also, it is to be understood that the milk or milk like product can be produced by suspending skim milk powder and/or full fat milk powder in an aqueous medium.

Also, it goes without saying that the concentration of $Ca^{++}$ is supposed to be of such value that $Ca^{++}$ is able to activate both the transglutaminase and the rennet.

Transglutaminase can be added in a dosage measured in g of pure transglutaminase per g of the protein content of the milk product, or in a dosage based on the transglutaminase activity unit, indicated in P. D. Bishop et al., Biochemistry, 29, 1990, pp. 1861–1869. Rennet can be added in a dosage based on the chymosin activity unit, indicated in IDF standard 110A, 1987.

Surprisingly it has been found that the rennet does not exert its normal function (separation of the milk in a cheese phase and a whey phase), but that a single phase gel product is produced as a result of the method according to the invention. Also, surprisingly it has been found that the gel is edible and exhibits satisfactory organoleptic properties, significantly differing from the properties of the acid products youghurt and junket. These organoleptic properties can be improved by addition of flavorants to the milk or milk like product.

Also, it is surprising that no emulsifying or stabilizing agents or only minor amounts thereof need to be added in relation to the method according to the invention. The reason for this is not completely understood, but it may be assumed as a hypothesis that the transglutaminase crosslinks the proteins in the milk or milk like product, whereby a lattice or network is generated, which do not need either emulsifying or stabilizing agents due to its own inherent stability.

From Japanese unexamined patent application JP-A 59-59151 (published Apr. 4, 1984) it appears that modified milk products in gel form can be obtained by addition of transglutaminase to milk. In this prior art method no rennet is added to the milk and also, the prior art product differs from the product produced by means of the method according to the invention.

From Japanese unexamined patent application no. 2276541 (published Nov. 13, 1990) it appears that a fibrous, tissue containing protein food can be obtained on the basis of a casein solution, transglutaminase and a milk coagulating enzyme. However, the process steps of this prior art method differs from the process steps of the method according to the invention, and also, the product resulting from this prior art process is not an edible gel.

In a preferred embodiment of the method according to the invention the transglutaminase is used in an amount of between 0.1 and 0.5% w/w, related to the amount of milk protein. In this manner an edible gel with satisfactory organoleptic characteristics can be obtained.

In a preferred embodiment of the method according to the invention the transglutaminase is of human, of bovine or of microbial origin. In this manner a transglutaminase with a satisfactory activity can be obtained.

In a preferred embodiment of the method according to the invention the milk or milk like product is whole milk, to which a flavorant has been added, preferably chocolate or vanilla flavor. In this manner an edible gel with superior organoleptic characteristics can be obtained.

In a preferred embodiment of the method according to the invention the rennet is Rennilase®, a protease derived from *Mucor miehei* and the rennet is used in an amount of between 1 and 30 Rennilase activity units/ml of milk or milk like product. In this manner an edible gel with satisfactory organoleptic characteristics can be obtained. Rennilase® is characterized in the Novo Nordisk product sheet "Cheese making with Rennilase" B250g-GB 2500 October 1990 PBz, and the Novo rennet unit is defined in IB 67/3-e, whereby both these publications are available on request from Novo Nordisk A/S, Novo Allé, DK-2880 Bagsvaerd, Denmark.

In a preferred embodiment of the method according to the invention the heat treatment is performed at a temperature between 60° and 140° C. and a time range between 1 and 20 minutes, preferably at a temperature between 70° and 100° C. and at a time range between 0.5 and 10 minutes. These intervals for temperature and time are optimal for gel formation.

Also, the invention comprises a use of the not acidified edible gel on milk basis producible by means of the method according to the invention, as a mousse, a cheese, or a pudding or as a pickling liquid for meat. In regard to the use as a pickling liquid for meat it is to be noted 1) that the transglutaminase and rennet containing milk or milk like product immediately before the heat treatment is injected into the meat or mixed intimately with the meat, and that the heat treatment is performed after the injection or the intimate mixing, and 2) that any kind of meat can be used in relation to this use, e.g. ham or fish meat. In relation to the use of the gel as a pickling liquid for meat it is to be noted that a gel cannot be injected into the meat; thus, in this case the third step of the method for production of the gel will only be performed after the injection of the transglutaminase and rennet containing milk or milk like product into the meat.

The method according to the invention and the use according to the invention will be illustrated in the following example.

EXAMPLE 1

To 500 ml of skim milk is added 7.5 ml of 1M $CaCl_2$, pH is adjusted to 7.0, and subsequently transglutaminase was added as 0.07 g of activated factor XIII. Thus the substrate is the protein in a concentration of approx. 3.5 g/100 ml. The total quantity is incubated at 37° C. for 45 minutes. Then 0.065 g of Rennilase® 50XL, corresponding to 6.5 RU/ml (RU is an abbreviation for Novo Rennet Units) is added, and the full amount is incubated at 37° C. for 45 minutes.

Of the thus produced transglutaminase and rennet treated skim milk 85.7 ml is mixed thoroughly with 4.0 g of cocoa, 10.0 g of sucrose and 0.3 g of vanilla, until the sugar is dissolved and the cocoa is suspended. The thus produced dessert is heat treated in a microoven. For an amount of 50 ml of dessert a microwave oven effect of 520 watt and a time of 60 seconds is used.

The functional and organoleptic characteristics of the dessert is fully satisfactory.

If a similar experiment without addition of rennet is performed, the end product remains liquid, and a phase separation takes place.

EXAMPLE 2

To 1000 ml of reconstituted skim milk, 9% dry matter, is added 5 ml of 1M $CaCl_2$, pH is adjusted to 6.3, and subsequently transglutaminase is added as 0.14 g of activated factor XIII. The total quantity is incubated for 60 minutes at 32° C. Then 0.250 ml Chymogen(R) corresponding to 4 RU/ml (RU is an abbreviation for Novo Rennet Units) is added, and the full amount is incubated for 30 minutes at 32° C.

The thus produced transglutaminase and rennet treated reconstituted skim milk is heated in a microwave oven in portions of 100 ml with an effect of 520 watt for 50 seconds.

The functional and organoleptic characteristics of the gels are fully satisfactory.

If a similar experiment without addition of rennet is performed, the end product remains liquid, and a phase separation takes place.

We claim:

1. A method for production of a non-acidified edible gel on milk basis, comprising:
   (a) adding a transglutaminase to milk or a milk-like product;
   (b) incubating the transglutaminase-containing milk product of step (a);
   (c) adding a rennet to the transglutaminase-containing milk or milk-like product of step (b); and
   (d) exposing the transglutaminase and the rennet-containing milk or milk-like product of step (c) to a heat treatment, and wherein an edible milk or milk-like gel is produced.

2. The method according to claim 1, wherein the transglutaminase added is between 0.1 and 0.5% by weight relative to the amount of milk protein.

3. The method according to claim 1, wherein the transglutaminase is of human, bovine or microbial origin.

4. The method according to claim 1, wherein the milk or milk-like product is whole milk to which a flavorant has been added.

5. The method according to claim 4, wherein the flavorant is chocolate or vanilla flavor.

6. The method according to claim 1, wherein the rennet is a protease derived from *Mucor miehei* and is used in an amount of between 1 and 30 Novo rennet units/ml of the milk or milk-like product.

7. The method according to claim 1, wherein the heat treatment is performed at a temperature between 60° and 140° C. and a time in the range of 0.5–20 minutes.

8. The method according to claim 7, wherein the heat treatment is performed at a temperature between 70° and 100° C. and at a time in the range of 1–10 minutes.

* * * * *